United States Patent [19]
Taguchi et al.

[11] Patent Number: 5,768,679
[45] Date of Patent: *Jun. 16, 1998

[54] ARTICLE MADE OF A TI-AL INTERMETALLIC COMPOUND

[75] Inventors: Kohei Taguchi; Michihiko Ayada, both of Kanagawa-ken; Hideo Shingu, Kyoto-fu, all of Japan

[73] Assignee: NHK Spring R & D Center Inc., Yokohama, Japan

[*] Notice: The term of this patent shall not extend beyond the expiration date of Pat. No. 5,580,665.

[21] Appl. No.: 707,349

[22] Filed: Sep. 3, 1996

Related U.S. Application Data

[63] Continuation-in-part of Ser. No. 148,438, Nov. 8, 1993, abandoned.

[30] Foreign Application Priority Data

Nov. 9, 1992 [JP] Japan ..................... 4-322226
May 13, 1993 [JP] Japan ..................... 5-134180

[51] Int. Cl.$^6$ ........................................ B22F 7/02
[52] U.S. Cl. .................. 428/548; 428/660; 75/245
[58] Field of Search ................ 75/249, 228, 245; 428/548, 660, 615

[56] References Cited

U.S. PATENT DOCUMENTS

| | | | |
|---|---|---|---|
| 4,292,077 | 9/1981 | Blackburn et al. | 75/175.5 |
| 4,294,615 | 10/1981 | Blackburn et al. | 75/175.5 |
| 4,331,477 | 5/1982 | Kubo et al. | 75/228 |
| 4,661,316 | 4/1987 | Hashimoto et al. | 420/418 |
| 4,668,282 | 5/1987 | Gilman et al. | 75/5 R |
| 4,668,470 | 5/1987 | Gilman et al. | 419/3 |
| 4,716,020 | 12/1987 | Blackburn et al. | 420/418 |
| 5,045,406 | 9/1991 | Huang et al. | 420/418 |
| 5,196,162 | 3/1993 | Maki et al. | 420/418 |
| 5,205,876 | 4/1993 | Sakai | 148/421 |
| 5,226,985 | 7/1993 | Kim et al. | 148/671 |
| 5,271,884 | 12/1993 | Huang et al. | 420/418 |
| 5,350,466 | 9/1994 | Larsen, Jr. et al. | 148/421 |
| 5,409,781 | 4/1995 | Rosler et al. | 428/547 |
| 5,417,781 | 5/1995 | McQuay | 148/671 |
| 5,429,796 | 7/1995 | Larsen, Jr. | 420/590 |
| 5,580,665 | 12/1996 | Taguchi et al. | 428/550 |

FOREIGN PATENT DOCUMENTS

| | | |
|---|---|---|
| 04-63237 | 2/1990 | Japan. |
| 02-101133 | 4/1990 | Japan. |
| 02-250931 | 11/1990 | Japan. |
| 03-199358 | 8/1991 | Japan. |
| 02-88343 | 4/1992 | Japan. |
| 04-124236 | 4/1992 | Japan. |
| 04-304 | 4/1992 | Japan. |
| 04-305 | 4/1992 | Japan. |
| 42-10408 | 11/1992 | Japan. |

*Primary Examiner*—Daniel J. Jenkins
*Attorney, Agent, or Firm*—Skjerven, Morrill, Macpherson, Franklin & Friel LLP; Alan H. MacPherson; Omkar K. Suryadevara

[57] ABSTRACT

An article essentially consisting of one or more of Ti-Al intermetallic compounds is fabricated so as to have a volume ratio of voids of 0.2 to 3.5% and a maximum size of voids less than 50 μm, by preparing a mixture of materials selected from a group consisting of Ti, Ti alloys, Al, Al alloys, and Ti-Al compounds, having a composition suitable for forming a desired Ti-Al intermetallic compound, and heating the mixture so that the mixture may be sintered. Typically, the temperature and pressure for the heating or sintering process, and the particle size of the material are appropriately selected so that a desired porosity and a desired range of void sizes may be obtained. The mechanical strength of the article according to the present invention is not only improved (as compared to the conventional Ti-Al intermetallic compounds) but is highly predictable, or, in other words, highly reliable. The fabrication costs can be reduced because the fabrication process involves only relatively low temperatures when simultaneously pressing and heating the article being formed. Furthermore, during the process of fabrication, such an article may have a highly favorable workability (as compared to the prior art) so that a final shape can be given to the article without involving any undue difficulty.

11 Claims, 3 Drawing Sheets

5,768,679

1

ARTICLE MADE OF A TI-AL INTERMETALLIC COMPOUND

CROSS REFERENCE TO RELATED APPLICATIONS

This is a continuation-in-part application of patent application Ser. No. 08/148,438 filed Nov. 8, 1993, now abandoned.

TECHNICAL FIELD

The present invention relates to an article made of a Ti-Al intermetallic compound which is easy to prepare but has a high mechanical strength.

BACKGROUND OF THE INVENTION

Ti-Al intermetallic compounds are attracting attention for various applications because the compounds are resistant to heat, acid and wear are extremely light-weight as compared to other such materials. Typical applications of Ti-Al intermetallic compounds include outer wall members which are exposed to high temperatures, and various engine components such as turbine components, pistons, and valve systems.

According to a known method for fabricating an article made of a Ti-Al intermetallic compound, a mixture of Ti and Al powders is heated to a temperature of approximately 1,300° C. under high pressure. It is also known to carry out a heat treatment to the thus fabricated article at a lower temperature to remove stress existing in the article. Also known is a process called self-propagation high temperature synthesis process (reaction synthesis process). According to this process, a mixture of Ti and Al powders is heated to a temperature higher than the reaction temperature so that the reaction is locally initiated. The heat resulting from the local reaction causes a chain reaction which propagates the reaction to the entire mixture so that an intermetallic compound can be obtained without melting the mixture.

It can be surmised that the ratio of the volume occupied by voids in an intermetallic compound or the porosity has a negative effect on the mechanical strength as is the case with other materials. However, the use of Ti-Al intermetallic compounds was started so recently that the relationship between the porosity and the mechanical strength has not been fully determined, and more research is needed to ensure a high level of reliability in applying Ti-Al intermetallic compounds to various mechanical components by allowing accurate prediction of the mechanical strength when the porosity is given. Japanese patent laid-open publications (kokai) No. 4-304 and No. 4-305 disclose the technology for fabricating spring seats and engine valve components with Ti-Al intermetallic compounds.

When a highly dense structure is to be attained in a Ti-Al intermetallic compound, it is necessary to process the compound at a high temperature and pressure. The process requires expensive special facilities and equipment to achieve such a high temperature and pressure. Furthermore, Ti-Al intermetallic compounds are known to be unsuitable for working. For instance, when a member made of a Ti-Al intermetallic compound is to be forged, an extremely high load is required. Therefore, conventionally, it was necessary to conduct special treatments to obtain a fine crystal grain structure (less than 15 μm), and forge the material at a temperature in excess of 1,000° C.

SUMMARY OF THE INVENTION

An article in accordance with the invention consists essentially of one or more of Ti-Al intermetallic compounds, wherein a ratio of the volume of voids existing in the article to the volume of the article, also called the "void ratio" is approximately 0.2 to 3.5%, the maximum size of the voids, called the "maximum void size" being less than 50 μm. More preferably, the void ratio is approximately 0.2 to 0.4%, and the maximum void size is less than 20 μm.

According to the experimental tests conducted by the inventors, it was found that a high bending strength can be achieved when the void ratio is approximately 0.2 to 3.5%, and the maximum void size being less than 50 μm, and that an even higher bending strength can be achieved when the void ratio is approximately 0.2 to 0.4%, and the void size less than 20 μm.

Typically, a lamella structure is predominant in an article in one embodiment of the present invention. According to the present invention, the article is preferably formed by heat treatment of a structure having at least a $\alpha_2$ phase and a $\gamma$ phase, the $\alpha_2$ phase being distributed like islands in a matrix of the $\gamma$ phase.

The Ti-Al compounds that are suitable as raw materials for the article may consist of TiAl powder, $Ti_3Al$ powder or the like. The raw-materials may be in various forms such as powder, foil, wire or the like. By appropriately selecting the diameter of the particles in the raw material, it is possible to control the size of the voids. The raw material may be pressed into an article (also referred to as a "compact") during the heating step by a quasi hot isostatic process (PHIP, quasi HIP or the like) using a pressure medium such as ceramics, a hot press process (HP), or a hot isostatic process (HIP). The conditions during heat treatment affect the final void size as well as the void ratio.

According to the experiments conducted by the inventors, it was found that the bending strength of Ti-Al compounds makes a marked change when the volume ratio of voids is approximately 3.5%, and a desired mechanical strength can be obtained by controlling the volume ratio of voids below 3.5%, preferably between 0.2 and 3.5% with the maximum void size less than 50 μm, most preferably between 0.2 and 0.4% with the maximum void size less than 20 μm.

Voids formed in the article generally have highly irregular shapes, and the void size as used in this application means a maximum dimension of a void. For instance, if the void is elliptic in shape, the size of this void is the dimension of the major axis. Reducing the porosity obviously improves the mechanical property of the article, but reducing the void ratio below 0.2% is technically difficult to achieve and is too expensive to be a practical choice. Material properties similar to a full density Ti-Al intermetallic compound can be obtained if the volume ratio of voids is no more than 0.4%.

According to a preferred embodiment of the present invention, to achieve such a volume ratio of voids, the heating step includes pressing the raw material while being heated to a temperature higher than 1,000° C. The pressing may be started any-time between the time when a to-be-formed compact is still at the room temperature before being heated and the time when the compact has been heated to a final temperature.

Mechanical strength of the mixture used to form a compact drops sharply when the temperature rises above 1,000° C. Therefore, voids can be easily collapsed at such a temperature. In this case, a HIP can be used, but a quasi HIP produces even better results because shear stress acts upon the material due to the anisotropicity of pressure, and the shear stress promotes the collapse of voids. The pressure applied during a heating step is normally high, but the pressure used in a quasi HIP process according to the present invention is in the order of 350 kgf/cm². The quasi HIP process as described herein forms a dense structure using a relatively low pressure, and is highly effective in reducing the fabrication cost.

According to a preferred embodiment of the present invention, the temperature for the heating step is higher than a temperature for melting the metallic phase of Al, and, following the heating step, a heat treatment process for diffusion is conducted at a temperature higher than the temperature for the heating step. In this case, the mixture for the compact may be pressurized continually from the room temperature to a temperature high enough to melt Al. However, a diffusion heat treatment process may be carried out without pressurizing the mixture.

It was determined by the inventors that the heating the compact to a temperature higher than the melting point of Al significantly increases the effectiveness of the diffusion heat treatment in removing voids from the structure. When the compact is heated to a temperature higher than the melting point of Al, and Al forms a liquid phase also called "liquid #1Phase"), it increases the effectiveness of pressure application in removing voids, and highly dense blocks are formed. Furthermore, in these blocks, most of the metallic Al phase eventually forms compounds, and almost no metallic Al phase remains because the reaction progresses more rapidly and compounds are formed more quickly in the liquid phase than in the solid phase. The liquid Al phase is prone to generation of voids due to the Kirkendall effect, but is rapidly eliminated by the heating process without substantially affecting the effectiveness in removing voids as a whole.

Thus, creation of a liquid AL phase is effective in forming a highly dense structure, and the heating speed is desired to be higher than 0.1° C./min. By increasing the heating speed higher than 10° C./min, a large amount of liquid phase is produced, and heat is rapidly generated so that voids are highly effectively removed as compared to a slower heating step. If the heating speed is less than 0.1° C./min, the reaction tends to progress before any liquid phase develops, and the liquid phase may not be generated to a sufficient degree.

In particular, as the reaction synthesis process tends to produce a large amount of gas from the surface of the compact due to the rapid temperature rise, the use of a quasi HIP is effective. A quasi HIP normally uses ceramics as a medium for pressurization therefore, the produced gas can be vented from the gaps between the ceramics particles. Thus, a quasi HIP allows the generated gas to escape while molding the mixture to form a compact of a complex shape, and thus promotes removal of voids. It is also possible to create a vacuum environment or other gas environment while pressing the mixture with ceramic powder. Such a vacuum environment or a gas environment can also be used with intermetallic compounds are used as the starting material.

When pure Al is used, the mixture is heated to at least 660° C. However, the temperature may vary for an alloy of #1 depending on the elements added to Al. Such as there are boron (B), manganese (Mn), tin (Sn) and nickel (Ni).

It is also possible to form an intermetallic compound by diffusion of Al in the solid phase even at a temperature below the melting point of Al. In this case, a small amount of metallic Al phase may remain in the structure, and reduce the reliability of the product. Therefore, it is desirable to use a temperature higher than the melting point of Al. By the intervention of the liquid phase of Al, voids are effectively removed, and the effect of pressing is improved. In particular, open voids which are connected to the surface can be readily removed, and even closed voids inside a compact can be readily removed by diffusion during a heat treatment process. Thus, the volume ratio of voids can be effectively reduced below 3.5% by the heat treatment process.

The γ phase mentioned in this disclosure mainly consists of fine crystals of TiAl, but may contain small amounts of Al₃Ti and Ti₃Al. The $\alpha_2$ phase mainly consists of fine crystals of Ti₃Al, but may contain small amounts of TiAl and metallic Ti. The lamella structure consists of alternating layers of TiAl and Ti₃Al, and is substantially homogeneous. The γ phase and the lamella structure are more resistant to heat than the $\alpha_2$ phase, and are therefore more preferable as a heat resistant, light-weight material.

The range of composition suitable for obtaining a structure essentially consisting of Ti-Al intermetallic compounds is Ti:Al=83:17 to 10:90 (at%), and the range of composition suitable for obtaining a lamella structure is 65:35 to 50:50 (at%). These figures may vary depending on the amounts and kinds of alloy elements which may be added.

BRIEF DESCRIPTION OF THE DRAWINGS

Now the present invention is described in the following with reference to the appended drawings, in which.

DETAILED DESCRIPTION OF THE PREFERRED EMBODIMENTS

Figure 1:
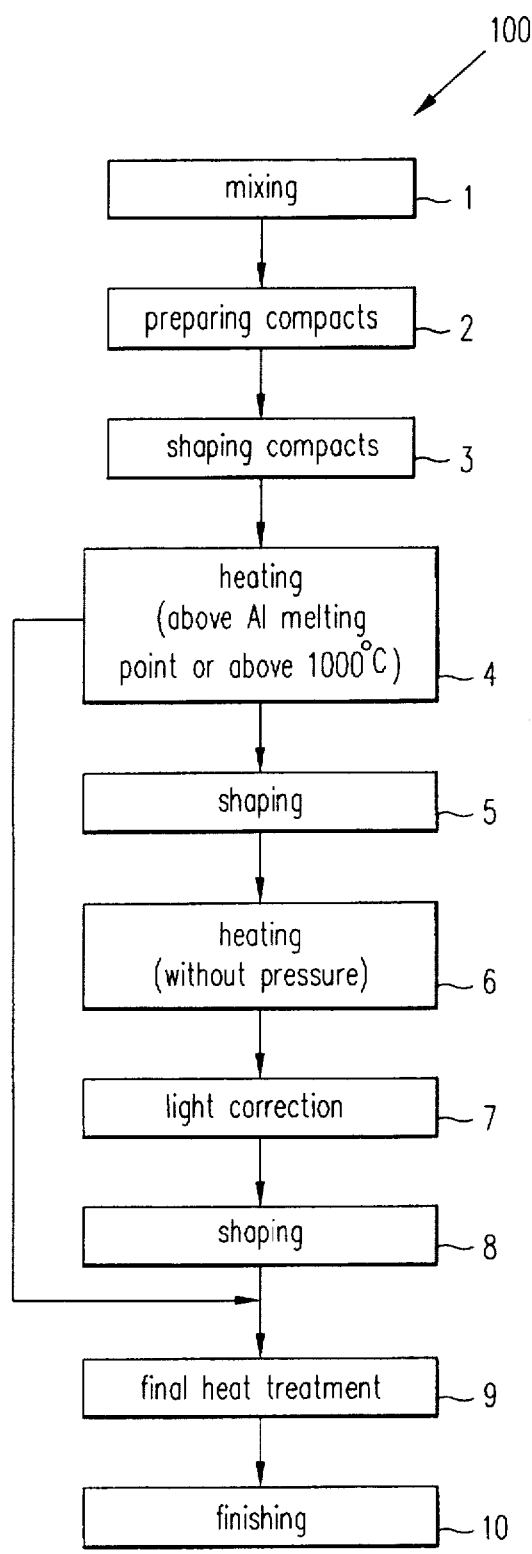
FIG. 1 is a flow chart showing an embodiment of the method of the present invention.

FIG. 1 shows steps 1–10 of a method 100 for fabricating an article according to the present invention. The steps 1 and 4 are indicated by solid line blocks and are essential steps for carrying out the present invention while the steps 2–3 and 5–10 are indicated by chain-dot line blocks and are non-essential steps which may be omitted depending on the embodiment.

Embodiment 1

In step 1, Ti or a Ti alloy is mixed with Al or an Al alloy at an appropriate composition ratio (described below) suitable for forming a desired Ti-Al intermetallic compound. It is also possible in other embodiments to mix two or more Ti-Al intermetallic compounds having different compositions (such as TiAl and Ti₃Al) in the form of powder. Alternatively, a mixture of Ti and Al may be mixed with a Ti-Al intermetallic compound. As a matter of fact, the mixture may consist of an arbitrary combination of Ti, Ti alloys, Al, Al alloys, and Ti-Al intermetallic compounds.

The starting material for carrying out the method may preferably be in the form of powder, foil, or filament, but may take other forms. The mixing in step 1 may consist of literally mixing a material consisting of two or more components so as to distribute them evenly among themselves, and the material may include a same component in two or more different forms. When the components are in the form of foil, layers of foil of different components may be interleaved as required.

In this embodiment, Al powder and sponge Ti powder both finer than 350 mesh and prepared by a gas atomizer process are mixed together at the weight ratio of Ti:Al= 65.8%:34.2% in a dry ball mill purged by Ar gas in step 1. The mixture prepared in step 1 is formed into a block of compressed powder or a compact in step 2 by applying pressure by using, for example, an extruder, a metallic die press, a hot press, a HIP machine, a CIP machine and if necessary, the compact was formed into a desired shape in step 3 by forging, machining or the like.

Figure 2A:
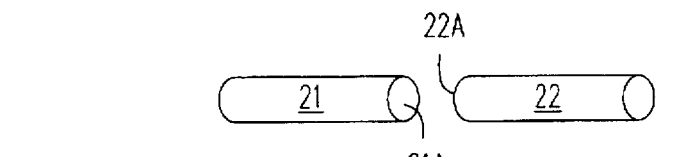
FIGS. 2A–2C illustrate how the four-point bending test can be carried out.

For instance, in step 2, the material mixture may be filled into a stainless steel tube (not shown), and compressed into a desired shape by carrying out a rotary swaging process on the stainless steel tube. Then, in step 3, the compact is machine into a cylindrical block 21 (FIG. 2A) of 8 mm in diameter and 20 mm in length.

According to an example where the separate steps 2 and 3 are omitted, the mixture prepared in step 1 is filled into a die mold, and both heat and pressure are applied to the mixture in a hot press or the like in step 4. Alternatively, the mixture may be filled into a capsule (not shown) to carry out a HIP process thereon.

In step 4, a pressure of 350 kgf/cm$^2$ is applied to the mixture by a quasi HIP temperature of 1,100° C., and was held for two hours at this temperature. In step 4, it is preferable to heat and press the mixture by a hot press, a HIP or a quasi HIP. Thereafter, the mixture is cooled to the room temperature. Throughout this step 4, the mixture is in a vacuum environment.

The workability of the mixture may improve if the mixture is molded in step 5 following the heating in 4 and before the heat treatment of step 6. More specifically, the inventors discovered that the workability indeed improved when the heating process of step 4 created a structure in which the $\alpha_2$ phase is distributed in the $\gamma$ phase like islands. Furthermore, the molding in step 5 offers the benefits of collapsing voids left from the heating in step 4, thereby adjusting the structure of the work piece. In another embodiment, the molding and the heat treatment in steps 5 and 6 are performed simultaneously. Thus, even when the porosity of the work piece after the completion of the heating of step 4 is greater than desired, the porosity may be suitably adjusted by the molding in of step 5 or the heat treatment in step 6.

A desired porosity can be also obtained by sintering the mixture of Ti powder and Al powder in step 4 through self-propagating high temperature synthesis without involving sudden heating, and then subjecting it to the molding step 5 or the heat treatment in step 6. Alternatively, a desired porosity can be obtained by preparing a mixture of TiAl powder or Ti$_3$Al powder or a mixture containing them, and heating the mixture in step 4. In this case also, the porosity can be further reduced by step 5 or heat treatment in step 6.

Figure 2B:
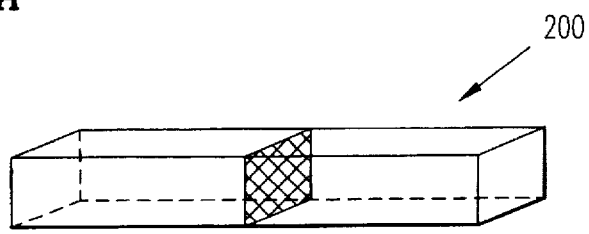

Next, a work piece 200 (FIG. 2B) is formed from a pair of cylindrical rod (8 mm in diameter and 40 mm in length), that are joined at the longitudinal ends surfaces 21A and 22A as illustrated in FIG. 4A. The opposing ends surfaces 21A and 22A are finished to smooth surfaces and are joined to each other by the process of thermal diffusion in a hot press at a temperature in the range of 750° to 900° C. in step 5 as a shaping process.

In the heat treatment of step 6 (FIG. 1), work piece 200 is heated to 1,200° C. in Ar gas flow approximately at the atmospheric temperature, and held at this temperature for two hours before they were cooled.

The heat treatment in step 6 is preferably carried out without substantially pressurizing the work in view of cost reduction. A primary purpose of this heat treatment in step 6 is the elimination of voids that were left from the heating in step 4, by diffusion. A secondary purpose of this heat treatment in step 6 is the adjustment of the structure that resulted from the heating in step 4. For instance, adjustment of the structure can include a diffusion step for uniformly distributing the components within the work piece 200, a heat treatment for adjusting the grain size of the crystals, a heat treatment step for recrystallization, and a heat treatment step for adjusting the structure through phase changes.

If the molded work piece 200 is slightly warped or otherwise deformed, a light correction step 7 may be performed on work piece 200. This correction step 7 typically consists of placing a weight on work piece 200, and can be therefore carried out simultaneously as the heat treatment in step 6. In the molding of step 8 following the heat treatment in step 6, a final working step such as forging, machining or the like is carried out. In step 9, heat treatment such as a precipitation hardening is carried out on the work piece 200 give work piece 200 a final shape. The finishing in step 10 typically consists of shot-peening, grinding or the like.

Figure 2C:
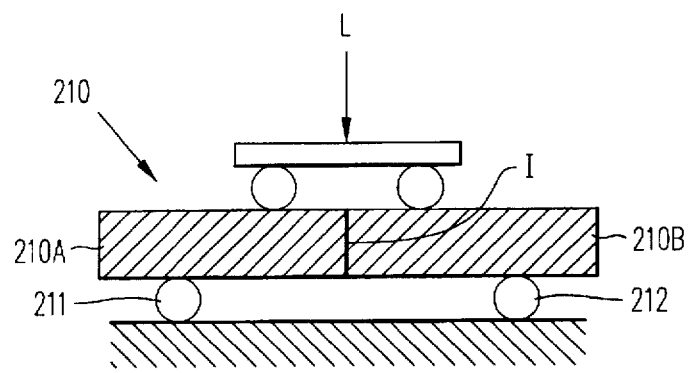
Figure 3:
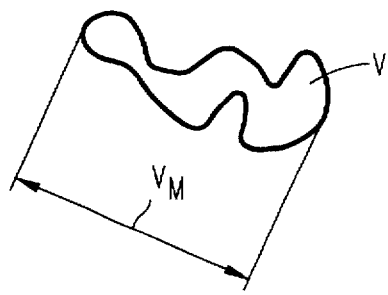
FIG. 3 is a diagram illustrating the definition of the void size.

Work piece 210 (FIG. 2C) can also be prepared from the rods 21 and 22 by grinding them into rectangular rods (3 mm×4 mm×38 mm), that are then joined as described above. Work piece 210 is subjected to a bending test by using an arrangement as illustrated in FIG. 3. The two portions 210A and 210B of the work piece 210 are simply supported by supports 211 and 212, and a load L is applied centrally to work piece 210 on two sides of interface I in the manner of a four-point bending test. Work piece 210 at the interface I in the middle when a sufficiently large load is applied. The ruptured surfaces (not shown) at interface I, when observed with an electron microscope have a number of voids, e.g. void V in FIG. 3. The inventors performed a number of such tests and measured the sizes of the largest voids near the starting point of the rupture. Table 1 relates the maximum size of a void to the bending strength of work piece 210. The void ratio within each work piece 210 was in the range of 0.2% to 0.4%, and the average void size was less than 15 μm. Reducing the void ratio below 0.2% involves difficulties which are not acceptable from practical view points. The ruptured surfaces at interface region I had a thickness of 20 μm, and the void ratio in this region was in the range of 0.2% to 3.5%. The maximum void size Vm (FIG. 4) in this region I ranged from 6.4 μm to 105.0 μm. The structure of each work piece 210 was that of a TiAl+Ti$_3$Al intermetallic compound, and its crystal grain size ranged from 10 μm to 30 μm, averaging 20 μm. The void size Vm is defined as a maximum dimension of void V as illustrated in FIG. 3.

The void size Vm of a sintered material can be controlled by appropriately selecting the particle size of the powder materials, the temperature at the time of the pressing step 3, the pressure for the pressing step, the temperature for heat treatment in step 4 and so on. The inventors have experimentally confirmed that the void size Vm below 50 μm can be obtained by selecting a particle diameter of less than 100 μm for the powder material, a pressure of 100 kgf/cm$^2$ or higher for the pressing step, and a temperature higher than the melting point (660° C.) of aluminum for the pressing step. The void size Vm can be reduced even further by conducting a heat treatment in step 4 at a temperature higher than 1,100° C.

TABLE 1

| void size (μm) | mechanical strength (kgf/mm²) | evaluation |
| --- | --- | --- |
| 105.0 | 44.9 | poor |
| 60.0 | 55.6 | poor |
| 49.0 | 61.9 | good |
| 47.0 | 65.0 | good |
| 28.0 | 63.4 | good |
| 18.0 | 74.3 | good |
| 38.6 | 62.0 | good |
| 49.0 | 66.6 | good |
| 75.0 | 50.2 | poor |
| 20.6 | 71.1 | good |
| 6.4 | 74.8 | good |
| 19.0 | 67.1 | good |
| 22.3 | 66.8 | good |
| 36.7 | 62.9 | good |

Embodiment 2

Figure 4:
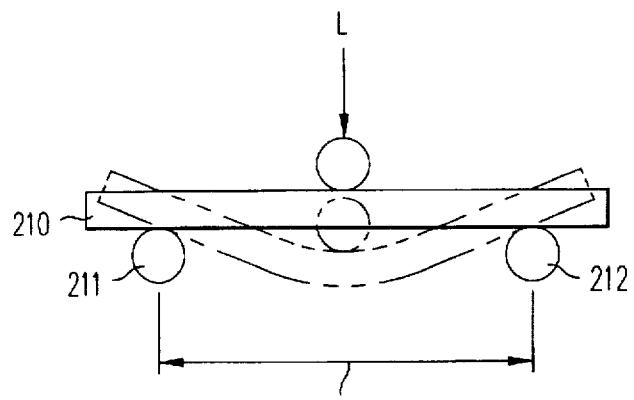
FIG. 4 is a diagram showing how the three-point bending test can be carried out.

Work pieces (e.g. work piece 410 in FIG. 4) each consisting of a block having dimensions of 4 mm×3 mm×40 mm were prepared in a similar manner as in Embodiment 1 except that the work pieces of Embodiment 2 consisted of solid blocks without any interface resulting from joining two blocks. The temperature for the quasi-HIP ranged from 600° C. to 1,000° C. The heat treatment lasted two hours at the temperature of 1,350° C. in Ar flow at the atmospheric pressure, and the work pieces were cooled to the room temperature. The obtained work pieces were subjected to a three-point bending test as illustrated in FIG. 4. The ruptured surfaces were observed with an electron microscope, and the maximum void sizes near the starting point of the rupture were measured. The relationship between the mechanical strength and the maximum void size is listed in Table 2.

The overall void ratio of the pieces ranged from 2.0% to 6.3%, and the average void size was less than 15 μm. The structure of each work piece was that of TiAl+Ti$_3$Al intermetallic compound, and consisted of a mixture of a γ phase and a lamellar structure, and the lamellar structure was predominant in the structure. The average grain size of the γ phase was approximately 20 μm. The average grain size of the lamellar structure was approximately 150 μm.

TABLE 2

| pressing temp. (°C.) | retaining Time (hrs) | maximum void size (μm) | mechanical strength (kgf/mm²) | void ratio (%) | evaluation |
| --- | --- | --- | --- | --- | --- |
| 1,000 | 1 | 13.0 | 64.8 | 1.98 | good |
| 900 | 1 | 23.0 | 62.7 | 2.21 | good |
| 750 | 6 | 34.5 | 66.7 | 3.17 | good |
| 750 | 1 | 26.0 | 63.3 | 3.10 | good |
| 600 | 6 | 54.0 | 59.5 | 6.31 | poor |

Figure 5:
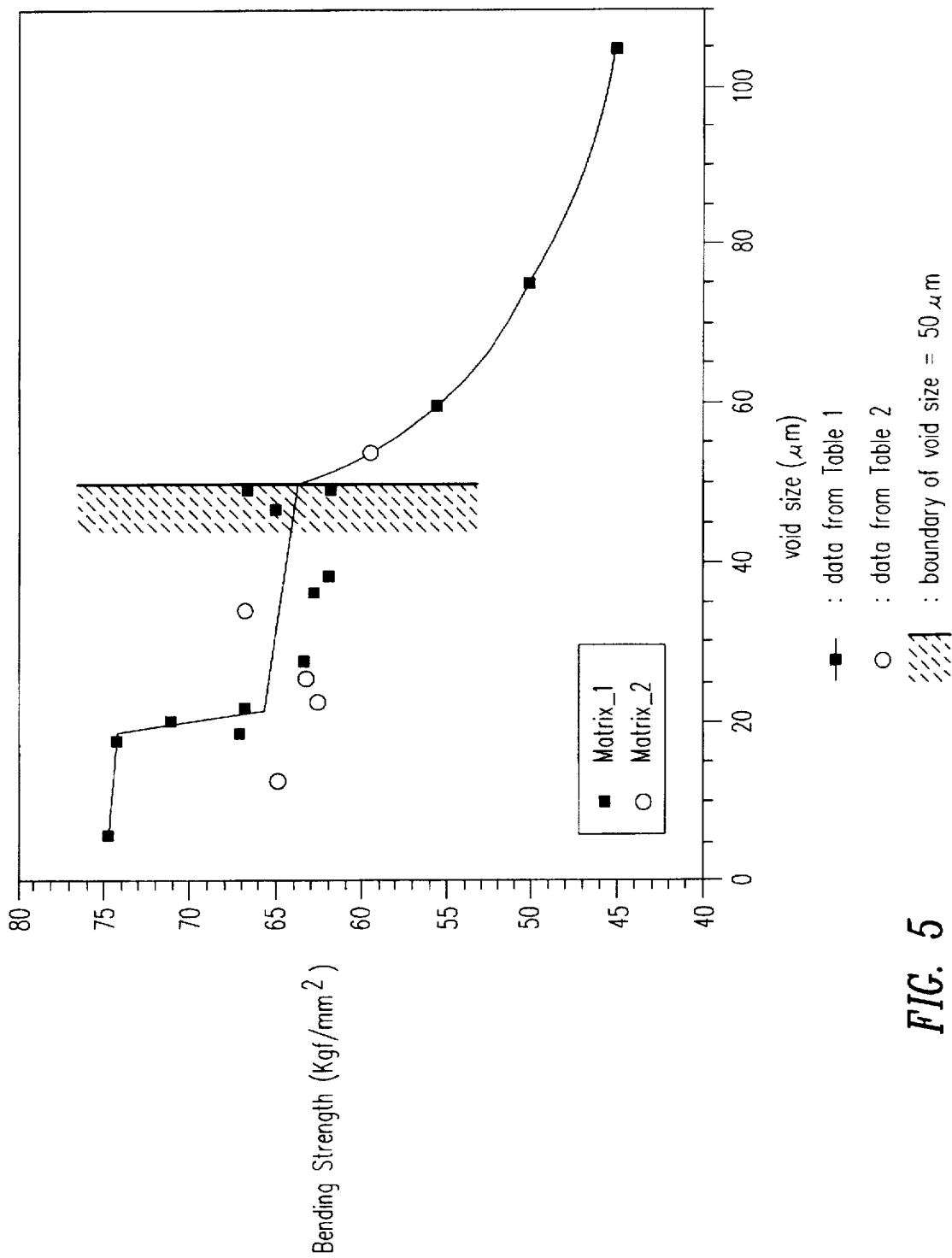
FIG. 5 is a graph showing the relationship between the maximum void size and the bending strength.

FIG. 5 is a graph summarizing Tables 1 and 2. From the above experimental results, the following conclusions can be drawn.

(1) By setting the maximum void size less than 50 μm while limiting the void ratio in the range of 0.2% to 3.5%, a high level of mechanical strength can be achieved. Even when the void ratio is at such a small level, limiting the maximum void size to less than 50 μm is still effective in ensuring a high mechanical strength. In other words, the void ratio is not the only factor in determining the mechanical strength, but the maximum void size also has a significant influence over the mechanical strength.

(2) By setting the maximum void size less than 20 μm while limiting the void ratio in the range of 0.2% to 0.4%, an even higher level of mechanical strength can be achieved. It can be seen from the graph of FIG. 5 that limiting the maximum void size to less than 20 μm is effective in improving the mechanical strength as far as Embodiment 1 is concerned but that it is not the case with Embodiment 2. It means that only when the void ratio is small enough to fall within the range of 0.2% to 0.4%, reducing the maximum void size to less than 20 μm is significantly effective in increasing the mechanical strength.

The present invention is effective in increasing the mechanical strength of intermetallic compounds including TiAl, Ti$_3$Al and/or (TiAl+Ti$_3$Al), but may be applicable to other Ti-Al intermetallic compounds. It is also anticipated that various properties may be improved by adding suitable amounts of various elements such as Si, Nb, Mn, Cr, V or the like, various compounds such as TiB$_2$, Y$_2$O$_3$, Ti$_5$Si$_3$, ceramics, intermetallic compounds or the like.

Thus according to the present invention, the mechanical strength of articles made of Ti-Al intermetallic compounds can be improved, and the fabrication costs can be reduced because the fabrication required for fabricating the article of the present invention involves only relatively low temperatures (as compared to the prior art) when pressing and heating the sample at the same time. The mechanical strength of the article according to the present invention is not only improved but is highly predictable, or, in other word, highly reliable. Furthermore, during the of fabrication, the work piece may demonstrate a highly favorable workability so that the final shape can be given to the work piece without involving any undue difficulty.

Although the present invention has been described in terms of specific embodiments thereof, it is possible to modify and alter details thereof without departing from the spirit of the present invention.

What we claim is:

1. An article essentially consisting of one or more of Ti-Al intermetallic compounds and having a plurality of voids, wherein a ratio of the volume of voids to the volume of said article is approximately 0.2 to 3.5%.

2. An article according to claim 1, wherein the ratio of the volume of voids existing in said article to the volume of said article is approximately 0.2 to 0.4%.

3. An article according to claim 1, wherein the average size of said voids is less than 15 μm.

4. An article according to claim 1, wherein a lamella structure is predominant in said article.

5. An article according to claim 1, comprising a lamella structure.

6. An article according to claim 1, wherein said article is formed by heat treatment of a structure having at least a first phase and a second phase, said first phase being distributed like islands in a matrix of said second phase.

7. An article according to claim 6, wherein said second phase consists of a γ phase.

8. An article according to claim 1, wherein at least one void is eliminated without applying any pressure during said heat treatment to form said article.

9. The article of claim 1 wherein the maximum dimension of each of said voids is less than 50 μm.

10. The article of claim 2 wherein the maximum dimension of each of said voids is less than 20 μm.

11. The article of claim 1 wherein said voids are left by elimination of at least one void by diffusion heat treatment during formation of said article.

* * * * *